United States Patent [19]

Bramm et al.

[11] Patent Number: 4,763,032
[45] Date of Patent: Aug. 9, 1988

[54] MAGNETIC ROTOR BEARING

[75] Inventors: Günter Bramm; Pavel Novak, both of Munich, Fed. Rep. of Germany

[73] Assignee: Fraunhofer-Gesellschaft zur Forderung der angewandten Forschung e.V., Munich, Fed. Rep. of Germany

[21] Appl. No.: 675,144

[22] Filed: Nov. 27, 1984

[30] Foreign Application Priority Data

Nov. 29, 1983 [DE] Fed. Rep. of Germany ........ 3343186

[51] Int. Cl.$^4$ .............................................. F16C 39/06
[52] U.S. Cl. .................................. 310/90.5; 128/1 D; 623/3
[58] Field of Search .......... 308/10; 128/1 D, DIG. 3; 623/3; 417/356; 340/870.32, 870.28, 870 R; 356/151

[56] References Cited

U.S. PATENT DOCUMENTS

| | | | |
|---|---|---|---|
| 3,623,835 | 11/1971 | Boyd | 310/90.5 |
| 3,787,100 | 1/1974 | Habermann | 308/10 |
| 3,791,704 | 2/1974 | Perper | 310/90.5 |
| 3,877,761 | 4/1975 | Boden | 308/10 |
| 3,929,390 | 12/1975 | Simpson | 310/90.5 |
| 3,938,913 | 2/1976 | Isenberg | 417/356 |
| 3,954,024 | 5/1976 | Staats | 310/90.5 |
| 3,957,389 | 5/1976 | Rafferty | 415/90 |
| 4,065,189 | 12/1977 | Sikorra | 310/90.5 |
| 4,147,396 | 4/1979 | Lyman | 310/90.5 |
| 4,180,946 | 1/1980 | Heikenskjold | 310/90.5 |
| 4,312,628 | 1/1982 | Yamamura | 310/90.5 |
| 4,392,693 | 7/1983 | Habermann | 310/90.5 |

FOREIGN PATENT DOCUMENTS

| | | |
|---|---|---|
| 0019313 | 2/1981 | European Pat. Off. . |
| 0060569 | 9/1982 | European Pat. Off. ............ 308/10 |
| 1472413 | 1/1969 | Fed. Rep. of Germany . |
| 2504631 | 8/1975 | Fed. Rep. of Germany . |
| 2342767 | 3/1978 | Fed. Rep. of Germany . |
| 2309754 | 11/1976 | France . |
| 0000987 | 11/1979 | Int'l Pat. Institute ................ 308/10 |
| 0003176 | 9/1982 | Int'l Pat. Institute ............. 310/90.5 |
| 2109596 | 6/1983 | United Kingdom ............... 310/90.5 |

OTHER PUBLICATIONS

W. Pschyrembol Klinisches Worterbuch, Dr. W. Kraus, Wide Gruyter, Berlin, New York, 1982, p. 378.
Textbook of Medical Physiology, A. C. Guyton, M.D., W. B. Saunders Co., Philadelphia, London, Toronto, 1976, pp. 158-175.

Primary Examiner—R. Skudy
Attorney, Agent, or Firm—Weingarten, Schurgin, Gagnebin & Hayes

[57] ABSTRACT

The present invention provides a magnetic rotor bearing for suspending a rotor in a contact-free manner, in particular the rotor of an axial- or radial-centrifugal blood pump, comprising a permanent- and electromagnet arrangement which stabilizes the position of, and suspends the rotor in a stator, in particular a housing, and comprises a circuit arrangement connected to at least one position sensor or to the position sensor operating circuit thereof for the rotor. The rotor is suspended in the stator in a stable, contact-free manner by means of a permanent magnet arrangement except for a single geometric adjusting degree of freedom. The position of the rotor is stabilized only within the geometric adjusting degree of freedom not stabilized by the permanent magnet arrangement, by a permanent magnet arrangement located in the rotor and comprising at least one permanent magnet. The permanent magnet arrangement which co-operates with the electromagnet arrangement comprises at least one permanent magnet of the permanent magnet arrangement provided for suspending the rotor and consists in particular, of the permanent magnets of this permanent magnet arrangement positioned in the rotor. The circuit arrangement is a control circuit stabilizing the position of the rotor, during the absence of external forces, in a position of minimum energy requirement of the electromagnet arrangement.

5 Claims, 4 Drawing Sheets

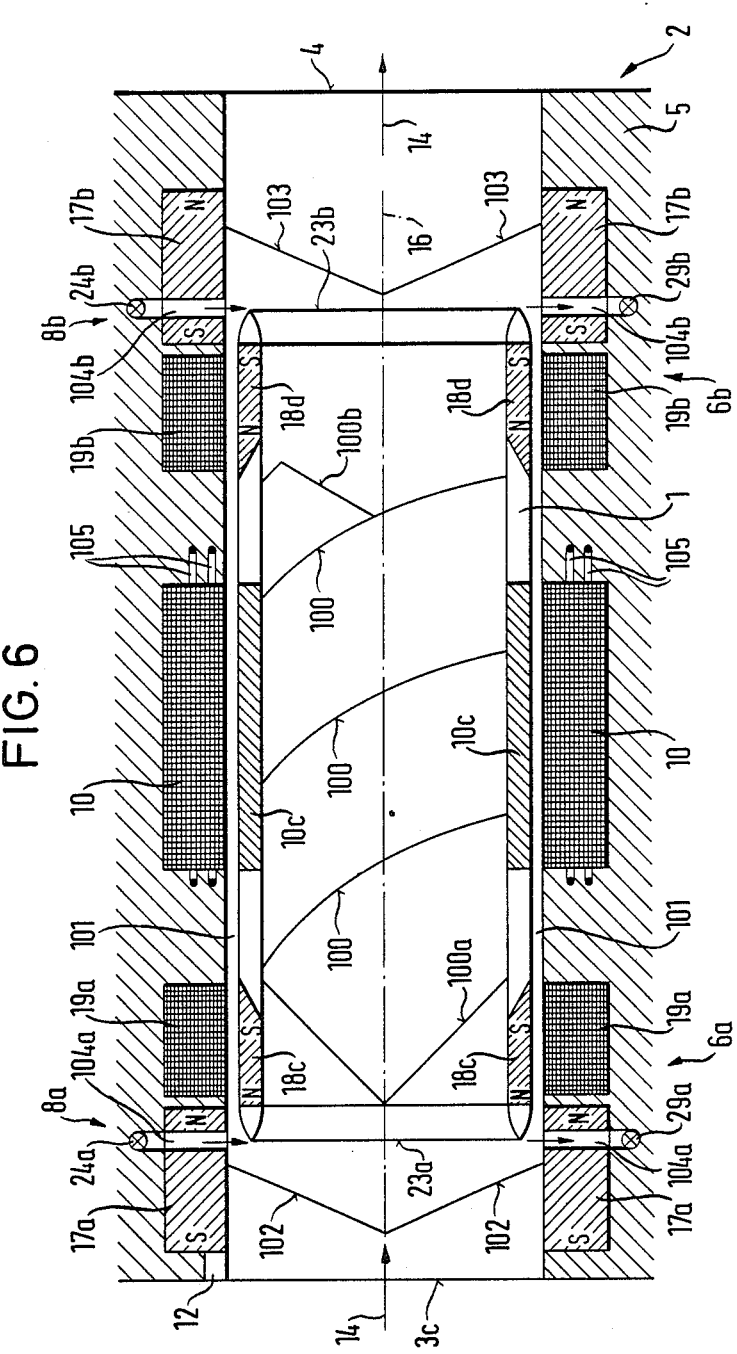

MAGNETIC ROTOR BEARING

BACKGROUND OF THE INVENTION

This invention relates to a magnetic rotor bearing for suspending a rotor in a contact-free manner, in particular the rotor of an axial- or radial centrifugal blood pump, comprising a permanent- and electromagnet arrangement which stabilizes the position of, and suspends the rotor in a stator, in particular a housing, and comprising a circuit arrangement which is connected to at least one position sensor for the rotor, to adjust the magnetic field of the electromagnet arrangement.

Although the magnetic rotor bearing according to the present invention has been developed for the rotor of an axial- or radial-centrifugal blood pump of an artificial heart, the use thereof is in no way restricted to such centrifugal blood pumps. Instead, it is also suitable for a variety of rotors which may be mounted by means of a contact-free magnetic suspension. Thus, the magnetic rotor bearing method including the relevent circuit arrangement connected to one or more position sensors, for adjusting the magnetic force of the electromagnet arrangement provided therein is also suitable for mounting and driving gyroscopes, for example, for the use thereof in space technology, during flight operations and in submarines or the like, and for gyro-directional stabilizers which are provided, for example, in rocket-propelled missiles, and for direct-reading instruments or the like.

Even with respect to its use in pumps, the magnetic rotor bearing which is provided according to the present invention is not restricted to axial- or radial-centrifugal blood pumps, but it may also be used in other blood pumps which have a rotor which may be suspended magnetically. Furthermore, the magnetic rotor bearing may also be used in other rotor pumps. For example, it may be used for particular advantage in rotor pumps for radioactiveliquids, because if such rotor pumps are provided with a magnetic rotor bearing according to the present invention, they are free of friction and thus of maintenance since they do not require any mechanical bearings, valves or seals etc. which are subject to wear.

Magnetic rotor bearings for suspending a rotor in a contact-free manner are known in various embodiments. Thus, U.S. Pat. No. 3,938,913 discloses a flowing device for pumping and/or measuring the flow of agressive, radioactive or particularly pure flowing agents, in which apparatus a rotor is suspended in a contact free, magnetic manner in a housing. Electromagnets are provided in the housing for suspending the rotor, which magnetic form in each case a magnetic circuit with magnetic material which is positioned in the rotor opposite the electromagnets. Only attractive forces are used in these magnetic circuits by which the rotor is held, suspended, inside the housing.

However, the use of exclusively attractive forces which are produced with electromagnetics suffers from considerable disadvantages:

(a) The stability of the magnetic bearing, i.e., the stability in the maintenance of the correct suspended position of the rotor, in which the rotor is positioned at an approximately equal distance in all radial directions from the inside wall of the housing, is most unsatisfactory with respect to self- and independently excited oscillations. A magnetic rotor bearing of this type tends towards oscillation relatively easily on account of the delayed built-up of the magnetic field. This delayed magnetic field build-up is a result of the relatively great inductances which are necessary to build up the complete magnetic field in each case by electric currents, and, because of the high permeability of iron ($\mu$ relative up to 10,000), high absolute inductances are produced which result in a delayed increase in the current.

(b) The energy consumption of such a magnetic rotor bearing having electromagnets is very high, and at the same time the efficiency is relatively poor, so that undesired thermal energy is produced to a considerable extent which is not only wasted and the dissipation of which is not only difficult, but is also extremely dangerous in the case of blood pumps, because blood albumen coagulates at 42° C.

(c) The specific forces are relatively low, as are the relative peak forces, because iron has a high density and fields which are essentially above 10 kilogauss produce saturation phenomena, $\mu$ relative approaching 1.

Furthermore, published European Application No. 0,060,569 or European Patent Application No. 82 102 188.8, disclose a magnetic rotor bearing which was previously developed, inter alia, by the inventors of the present magnetic rotor bearing, for suspending a rotor of a centrifugal blood pump in a contact-free manner. In that bearing, a combined electromagnet- and permanent magnetic arrangement is provided for suspending the rotor, which arrangement consists of electromagnets which are provided in the stator forming the housing of the centrifugal blood pump, and consists of permanent magnets which are positioned in the rotor opposite the electromagnets, so that they co-operate with the electromagnets.

This combined electromagnet- and permanent magnet arrangement basically suffers from the same disadvantages as have been mentioned above in connection with the magnetic rotor bearing according to U.S. Pat. No. 3,938,913. The exclusive use of electromagnets in the stator leads to a relatively high energy consumption and thus to a considerable generation of heat, and moreover, a relatively unsatisfactory stability results on account of the delayed field build-up which is inherent to electromagnets.

SUMMARY OF THE INVENTION

In contrast thereto, the present invention provides a magnetic rotor bearing of the initially mentioned type which meets in particular the following two requirements:

(1) The magnetic rotor bearing should have a high an electromechanical efficiency as possible, so that the proportion of energy which is expended for the magnetic suspension and position stabilization of the rotor and which is converted into heat is as small as possible in percentage terms and thus the operating temperature remains restricted to values which are as low as possible, in particular, to values which lie below the temperature at which the blood albumen starts to coagulate.

(2) The absolute energy requirement of the magnetic rotor bearing should be as low as possible, so that the absolute amount of energy which is converted into thermal energy on account of the magnetic suspension and stabilization of the rotor, is as low as possible and thus, moreover, each element of the entire magnetic rotor bearing is as small as possible, which is important particularly if the magnetic rotor bearing is to be used in a centrifugal blood pump which is to be implanted, in particular with respect to the fact that even a small reduction in the energy requirement of the centrifugal blood pump itself results in a considerable reduction in the weight, the volume and the energy requirement of the entire centrifugal blood pump arrangement which is to be implanted and which comprises, in addition to the centrifugal blood pump, a control circuit and, for example, an energy converter or store and an inductive energy coupling device for coupling energy into the implanted centrifugal blood pump arrangement.

The objectives are achieved according to the present invention with a magnetic rotor bearing of the initially mentioned type, in that:

(a) the rotor is suspended in a stable, contact-free manner in the stator except for a single geometric adjusting degree of freedom, by means of a permanent magnetic arrangement which comprises at least one permanent magnet positioned in the rotor and at least one permanent magnetic positioned in the stator;

(b) the position of the rotor is stabilized only within the geometric adjusting degree of freedom which is not stabilized by the permanent magnetic arrangement, by means of an electromagnetic arrangement which is provided in the stator and comprises at least one electromagnet, and by means of a permanent magnet arrangement which co-operates with the electromagnetic arrangement, which is located in the rotor and which comprises at least one permanent magnet;

(c) the permanent magnet arrangement co-operating with the electromagnet arrangement; at least one permanent magnet of the permanent magnet arrangement provided for suspending the rotor, and consists in particular of the permanent magnets of this permanent/magnetic arrangement positioned in the rotor; and (d) the circuit arrangement is a control circuit which stabilizes the position of the rotor, during the absence of external forces, in a position of minimum energy requirements of the electromagnet arrangement.

The function according to (d) is performed by a control loop having a fixed desired value.

This magnetic field bearing according to the present invention has as high an electromechanical efficiency as possible, because only the smallest possible proportion of the magnetic forces required for suspending and stabilizing the rotor is produced electromagnetically, whereas by far the greatest proportion of the magnetic forces required is supplied by means of permanent magnets. In this connection, it is pointed out that a stable suspension of the rotor by means of permanent magnets is impossible by the Earnshaw Theorem alone, according to which each mechanical system which is held balanced in space (3 dimensions) only by means of permanent magnets is unstable. Moreover, the absolute energy requirement of the magnetic rotor bearing according to the present invention is as small as possible, because the control circuit stabilizes the rotor in a position in which the absolute energy requirement of the electromagnet arrangement is minimised without external forces, whereas in order to minimise the energy requirement during the effect of external forces, a superimposed regulator which is specified below may be provided.

Thus, the magnetic rotor bearing according to the present invention is most advantageously suitable for all cases in which the energy requirement of a magnetic rotor bearing of this type should be absolutely and relatively low and, moreover, the increase in temperature which the magnetic rotor bearing experiences due to the heat which is generated should be as low as possible.

Consequently, the magnetic rotor bearing according to the present invention may be used particularly advantageously in blood pumps, in particular axial- and radial centrifugal blood pumps, above all in those cases in which blood pumps of this type are to be implanted. The relatively low generation of heat makes it possible to remain safely below the temperature of 42° C. at which blood albumen starts to coagulate and which is therefore extremely dangerous to the human blood circulation.

A particularly preferred embodiment of the magnetic rotor bearing according to the present invention which is stated above is distinguished in that:

(1) the permanent magnetic arrangement suspending the rotor comprises a stationary permanent annular magnet which is positioned concentrically to the axis of the rotor, which is magnetized in the axial direction of the rotor, and further comprises a permanent bar or annular magnet which is axially displaced with respect to the permanent annular magnet, but is positioned concentrically with that magnet about the axis of the rotor and is magnetized in the axial direction of the rotor, and magnetic poles as the same kind of the permanent annular magnet of the stator and of the permanent bar or annular magnet of the rotor face one another;

(2) the electromagnet arrangement has an axial electromagnet inside which the permanent bar or annular magnet of the rotor is positioned, and (3) the circuit arrangement is a control circuit which is connected at its actual value input to the position sensor which determines the axial position of the rotor.

As a result of this permanent magnet configuration according to the present invention, maximum centering forces are present in a radial direction with a given size of the magnet material or of the magnet arrangement, in particular with a given quantity, a given volume and a given weight of the magnet material or the magnet arrangement.

The permanent magnetic arrangement according to the present invention is preferably constructed as follows:

(1) With a given cross section of the permanent magnets, the length thereof is to be selected such that the maximum external leakage flux can develop. To this end, the length of the permanent magnet must be selected such that the magnetic voltage which is present is just sufficient for driving the leakage flux through the magnetic resistance in the leakage field region or volume.

(2) Rare earth magnets, in particular cobalt-samarium magnets are preferably used as the permanent magnet material. This material is weakened or demagnetized to the smallest extent under the influence of a magnetic stray field. Moreover, a high magnetic voltage is achieved at the shortest magnetic length. Finally, the specific magnetic energy of the material, based on the weight, is the greatest of all magnet materials. Finally, the homogeneity of the magnetization of the material is relatively good.

(3) The external diameter of the permanent bar or annular magnet of the rotor must lie within the order of magnitude of the internal diameter of the permanent annular magnet of the stator and must be slightly smaller than this diameter. Consequently, maximum change, based on the unit of length of the displacement, of the entire magnetic field energy of the permanent magnet arrangement takes place, for example in the case of a radial displacement of the rotor permanent magnet, with respect to the stator permanent magnet.

(4) Only extremely homogeneous magnetic material is used, because otherwise the rotor rotates eccentrically, since the axis of symmetry of the magnetic field would not otherwise coincide with the geometrical axis of the magnet.

In the permanent magnet arrangement according to the present invention, merely the axial degree of freedom requires a stabilization in order to stabilize the entire magnetic rotor bearing, and this stabilization is effected by the above-mentioned electromagnet arrangement which has an axial electromagnet. An essential feature of the permanent magnetic-electromagnetic mixed construction according to the present invention is the interaction, which takes place in this case, between the permanent magnetic field and the electromagnetic field, by which the axial degree of freedom is stabilized by the electromagnet in that the field intensity of this electromagnet is controlled by a control loop which comprises a position sensor device determining the position of the axis of the rotor in an axial direction, and by which a signal is produced which indicates the actual position of the rotor axis in the axial direction and is compared in the control loop with a desired value indicating the desired position of the rotor axis in the axial direction, whereupon the control circuit of this control loop regulates the electrical supply to the electromagnet such that the axial position of the rotor axis is brought into the desired position and is held therein.

A particular rapid reset of the rotor axis into the desired position when the rotor axis is moved out of this desired position by any forces, is achieved in that, in an embodiment of this invention, the control circuit has an output amplifier which controls in a current proportional manner. Consequently, the current in the exciting coil of the electromagnet may be adjusted within a very short time to a specific current value necessary for returning the rotor axis to its desired axial position. As a result of this, a delay in the field build-up by the inductance of the electromagnet may be eliminated.

The above-mentioned control with a fixed axial desired position of the rotor is indeed optimum for short-term external adjusting forces acting on the rotor, with respect to the energy consumption, because such short-term forces disappear again according to definition after a relatively very short time, namely after a few 1,000th, 100th or 10ths of a second. However, if external axial adjusting forces act on the rotor axis in the long term, i.e. from a few tenths of a second to a few hours, a substantially increased energy consumption may be produced for the stabilization of the rotor axis in the above-mentioned desired position. In order to reduce this increased energy consumption, a particularly preferred embodiment of the magnetic rotor bearing is designed according to the present invention such that the control circuit has a superimposed regulator which moves the motor position by the control circuit during the long-term influence of substantial external forces, directly or indirectly by changing the actual value of the position sensor, and which reduces, preferably minimizes, the energy consumption of the magnetic rotor bearing. Experiments on practical embodiments of the magnetic rotor bearing according to this invention have shown that the energy requirement of this magnetic rotor bearing amounts to about, for example 0.1 Watt for the position regulation of the rotor axis in the absence of substantial external forces, and this energy requirement may increase up to, for example 10 to 15 Watts during the effect of substantial external forces, i.e. increases by 100 to 150 times if the above-mentioned superimposed regulator is not provided. Substantial external forces are, in particular, unilaterally acting acceleration forces, of the type which arise, for example in motor vehicles, trains and aeroplanes or the like during starting up and braking, as well as acceleration due to gravity as long as it becomes very asymmetric with respect to the axial direction of the rotor, which may happen, for example if a patient who hse, implanted, an artificial heart with a rotor which is mounted by means of the magnetic rotor bearing according to the present invention, sleeps on his side or the like. When it is considered that in the case of such an implanted artificial heart, the power which is required has to be coupled inductively into the body of the patient, it is most essential for the power required for stabilizing the position of the rotor to amount to only about 0.1 Watt instead of, for example from 10 to 15 Watts, as mentioned above.

The superimposed regulator preferably comprises the following devices in particular:

(a) a detection device detecting the presence of external forces;

(b) an adjusting device moving the rotor out of its stabilized centre position into an eccentric stabilization position; and (c) a comparison device comparing the energy requirement of the rotor bearing in the stabilized centre positions with its energy requirement in the eccentric stabilization position.

A superimposed regulator which is constructed in this manner therefore operates if the detection device detects substantial external forces, such that this deivce causes the adjusting device to move the rotor out of the previous stabilized centre position some way into an eccentric stabilization position, so that permanent-magnetic forces of the bearing magnets which arise in an asymmetric position of the rotor counteract the external forces.

Thereupon, the comparison device compares the previous energy requirement with the new energy requirement of the magnetic rotor bearing, and depending on whether the new energy requirement is higher or lower than the previous energy requirement, the adjusting device moves the rotor again in a following step in the sense of a reduction of the energy requirement of the magnetic rotor bearing, and this gradual or continuous adjustment is preferably effected until a new stabilization position of the rotor axis is achieved in which the magnetic rotor bearing has a minimum energy requirement under the respective substantial external force.

By means of a corresponding response delay, it is possible for the superimposed regulator not to respond to short-term external forces, for example, such forces which last for only fractions of seconds.

Although the most varied kind of detection devices are suitable for a superimposed regulator of this type, a current meter for measuring the electric current flowing through the electromagnet arrangement is preferably used as the detection device, or a currnet meter for measuring the complete electric current which flows through the control loop comprising the position sensor or sensors, the control circuit and the elecromagnet arrangement.

A preferred embodiment of the adjusting device is a position sensor-desired value changing device, in which case this desired value, which corresponds to the desired axial position of the rotor axis, may either be directly changed in that the desired value fed into the control loop is changed accordingly, or indirectly in that the desired value fed into the control circuit is maintained constant, but an additional quantity is added to the actual value released by the respective position sensor or an additional quantity is subtracted from this actual value.

Finally, the comparison device preferably comprises a current meter for measuring the electric current flowing through the electromagnet arrangement or through the complete control loop, and a sample- and hold circuit which memorizes and compares the measured values of the current. A delay member may possibly also be used for this purpose as long as the value is held for a sufficient period.

The most varied position sensors which are known according to the prior art may, in principle, be used as position sensors, as long as the position information is present only in the stator and as long as a sensor part which may be in the rotor, does not require energy or an electrical contact. However, magnetic field sensors cannot generally be used (magnet in the rotor), because such sensors may be influenced by the magnetic field of the magnetic rotor bearing and consequently unfavourable reactions result. Capacitive sensors for determining position are unusable in practice or are very problematic for different reasons, and that is, firstly, because an electric field is thereby produced in the blood and a problematic contacting is necessary, if the capacitor plates of a sensor of this type are provided between the stator and the rotor, and secondly, because in those cases in which the two capacitor plates of the sensor are provided on the housing, a change in the dielectric takes place between these capacitor plates due to the rotor. According to the present invention, radiation sensors are preferably used as position sensors, in particular such radiation sensors which operate with light radiation or sound radiation, preferably infrared sensors or ultrasonic sensors.

In particular, the magnetic rotor bearing according to this invention is preferably constructed with respect to its position sensor arrangement such that the position sensor comprises at least one pulse radiation nbarrier which is operated by the rotor shaft and has a pulse-controlled radiation transmitting element and a radiation receiving element.

The position sensor device which preferably has two position sensors and a position sensor operating circuit connected thereto may, in particular, comprise the following:

(1) two pulse radiation barriers, each of which cooperates with an axial end of the rotor shaft;

(2) a subtraction device subtracting the output signals of the radiation receiving elements of the two pulse radiation barriers;

(3) an integration device integrating the output signals of the subtraction device;

(4) a sample- and hold circuit connected to the output of the integration device; and (5) a delivery control device for controlling the closing and opening stroke of a first, second and third switch, of which the first switch is provided between the output of the subtraction device and the input of the integration device, while the second switch is a switch causing the reset of the integration device, and the third switch is positioned between the output of the integration device and the input of the sample-and hold circuit, and the delivery control device controls the closing times of the three switches such that the first switch is always closed when the radiation transmitting elements are transmitting, whereas the third switch is closed in each case after the integration of a predetermined number of output signals from the subtraction device, and the second switch is closed each time the third switch is opened.

As already emerges from the statements made above about the sensors preferably used, the pulse radiation barriers are preferably either infrared light barriers or ultrasonic barriers. The advantage of infrared sensors or infrared light barriers and of ultrasonic sensor or ultrasonic barriers resides in particular in the fact that both types of these sensors or barriers are decoupled from the electric or magnetic properties of the surroundings, because infrared light or ultrasonic radiation is virtually unaffected by these electric or magnetic properties. Apart from this, the LED diodes used during the employment of infrared light have a very low energy requirement, are low in price and small.

In connection with the magnetic rotor bearing described above or irrespective thereof, an asynchronous motor may be provided as the drive of the rotor, which motor is connected to an oscillator as the operating voltage source, the frequency and output voltage amplitude of which may be changed depending on the load and speed, such that the torque released by the asynchronous motor correlates with the moment of the load at the respective speed of the synchronous motor, in particular, the respective moment of the load of the rotor on the motor characteristic line of the asynchronous motor lies slightly below the breakdown torque and above the breakdown speed.

An electronically commutated direct current drive is also particularly advantageous. To this end, permanent magnets, in particular, in the form of magnetic discs or other magnetized areas in the rotor, may preferably be provided around the outer periphery of the rotor or inside its outer periphery, as alternating magnetic poles, which are opposite wire coils in the stator which are bilaterally or unilaterally iron free and through which current flows and which detect as far as possible the total magnetic flux of the above-mentioned permanent magnets of the rotor, the electric current in the wire coils being commutated such that the rotor is made to rotate.

If the rotor is used as a conveying member in a blood pump, in particular a centrifugal blood pump, a power control device may be provided which comprises the following:

(a) a pressure sensor on the suction side of the blood pump;

(b) a characteristic memory which is connected by its input to the pressure sensor and assigns and releases a specific output quantity to a predetermined input quantity; and (c) a power control device controlling the actual blood pumping power corresponding to the output quantity of the characteristic memory, preferably an oscillator, the frequency and output voltage of which may be changed depending on the load and speed and which is connected to an asynchronous motor which drives the blood pump, as the operating voltage source of this asynchronous motor.

Although a magnetic rotor, of the type provided by the present invention, is preferably driven in the manner described above, as an alternative, the drive mechanism may also be designed in any other suitable manner, for example, as a synchronous motor, an electronically commutated electromotor which is excited by permanent magnets, etc.,. Furthermore, although the above-described asynchronous motor drive is preferably used in the case of a rotor which has a magnetic rotor bearing designed according to the present invention, this asynchronous motor drive may also advantageously be used in the case of differently mounted rotors, for example, in such rotors which are mounted magnetically only by means of electromagnets, or in rotors which have a mixed electromagnetic-permanent magnetic rotor bearing of the type described in U.S. Pat. No. 3,938,913 and in Published European Application No. 0,060,569, or in the case of any other magnetic, mechanical or hydraulic rotor bearings etc.

BRIEF DESCRIPTION OF THE DRAWINGS

The present invention, as well as other advantages and features thereof will now be described in more detail in the following with reference to FIGS. 1 to 5 of the drawings using a few particularly preferred embodiments of the rotor bearing according to the present invention and using a preferred embodiment of a rotor drive of this invention.

FIG. 6 shows an embodiment of an axial-centrifugal blood pump according to the present invention.

DETAILED DESCRIPTION OF THE INVENTION

Figure 1:
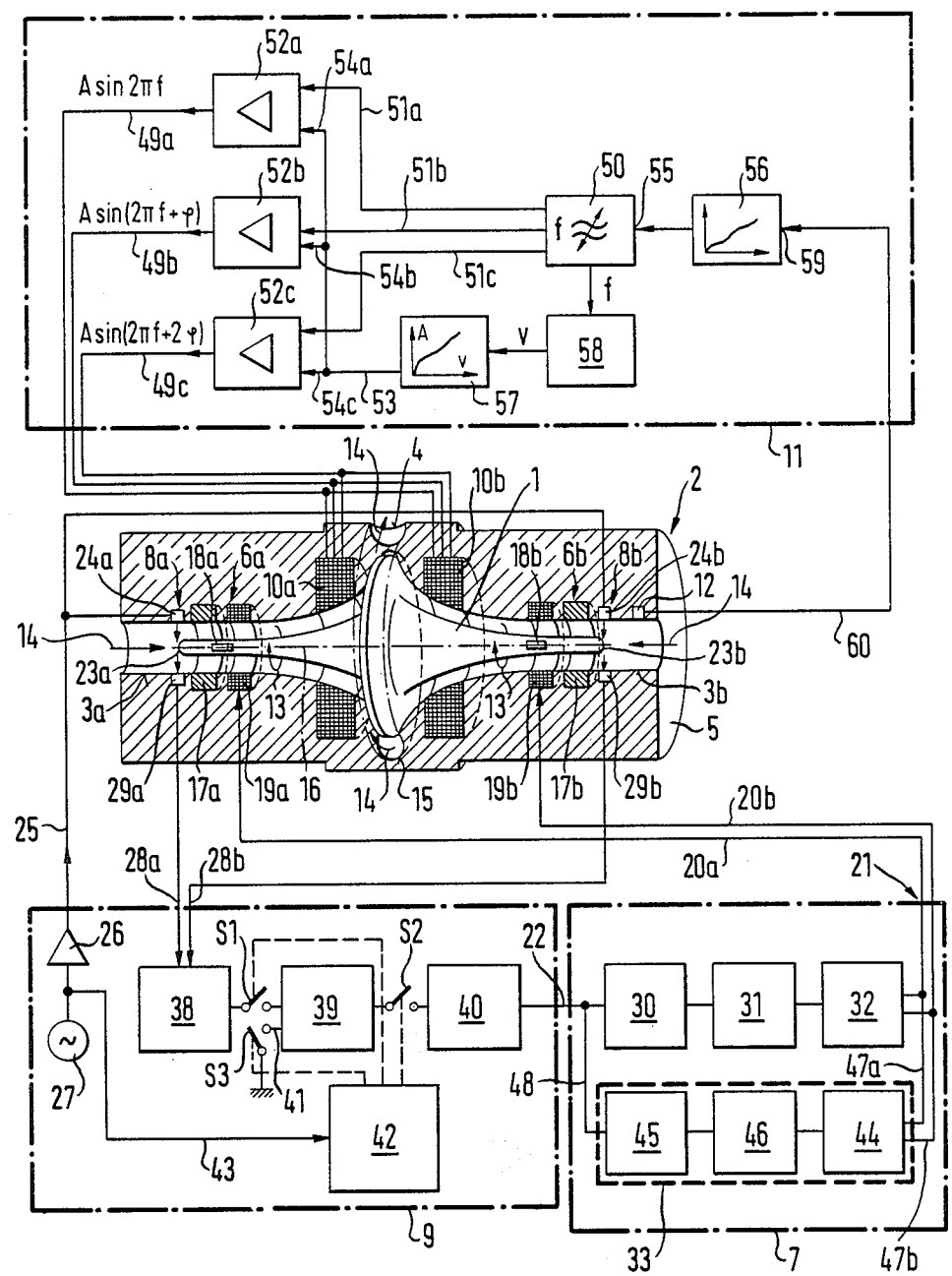
FIG. 1 is an overall view of a particularly preferred embodiment of a magnetic rotor bearing according to the present invention and of a rotor drive of this invention, of a rotor of a double-flow radial-centrifugal blood pump, shown in a perspective view, together with the permanent and electromagnets in which the rotor of this centrifugal blood pump is mounted or driven in a magnetic contact-free manner, while the control circuit of the magnetic rotor bearing and the drive circuit for the rotor are shown in a block view.

The magnetic rotor bearing and the rotor drive shown in FIG. 1 are used in this case for mounting and driving the rotor 1 of a double-flow radial-centrifugal blood pump 2 which has two blood in-flow channels 3a and 3b and one blood outlet 4 formed in a stator 5 serving as the housing of the centrifugal blood pump 2, the rotor 1 being mounted in the stator 5 in a magnetic, contact-free manner.

The magnetic rotor bearing comprises a first and a second permanent- and electromagnet arrangements each generally indicated by 6a and 6b respectively, each surrounding one of the two axial end regions of the rotor 1, and a control circuit 7 for operating the electromagnets of the permanent- and electromagnet arrangements 6a and 6b. Moreover, the magnetic rotor bearing comprises two position sensors, designed in each case as pulse radiation barriers 8a and 8b for determination of the axial position of the rotor 1, and a position sensor operating circuit 9 which receives input signals from the pulse radiation barriers 8a and 8b, and releases a corresponding output signal to the control circuit 7.

The rotor drive comprises two driving electromagnets 10a and 10b, which, together with the metallic body of the rotor 1 form as asynchronous motor, and comprises a power control device 11 having a pressure sensor 12 positioned on the suction side of the centrifugal blood pump 2, here, in the blood in-flow channel 3b. The rotation of the rotor 1 is indicated by arrows 13, and the blood flow by arrows 14.

The rotor 1 together with its shaft which may consist of, for example polished aluminium, is hollow inside, so that its total density is exactly adapted to that of the blood surrounding it. The flow of blood is guided through the two blood in-flow channels 3a and 3b from both sides to the disc-shaped rotor 1 and is driven by the rotor 1 centrifugally via an annular blood channel 15 and centrifugally out of the stator 5 serving as the housing, so that consequently no asymmetric forces arise on the rotor 1 due to the operation thereof.

In one embodiment given by way of example, the energy requirement of the rotor drive is from about 8 to 10 Watts under a constant blood pressur of 0.133 bars, and is thus substantially lower than that of blood pumps which operate in a pulsating manner. In this embodiment, the energy requirement of the magnetic rotor bearing is only about 0.5 Watts. On account of this low energy requirement, the sets of batteries or accumulators for the energy supply may be relatively small and light and may be implanted, and only have to be renewed after one or two days, or, for example, recharged at night.

Figure 2:
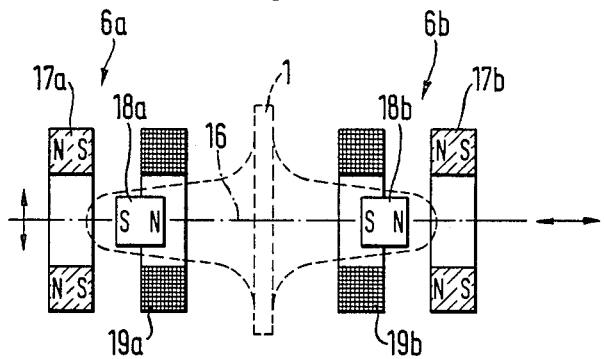
FIG. 2 is a sectional view through a magnet arrangement for the magnetic bearing of a rotor of a blood pump according to FIG. 1, the motor being indicated in dashed lines.

In particular, the permanent- and electromagnet arrangements 6a and 6b of the magnetic rotor bearings which are shown in FIG. 2 on an enlarged scale as compared with FIG. 1, are designed such that the rotor 1 is suspended in a stable, contact-free manner in the stator 5 FIG. 1 in the region of each of its two axial ends by means of a rotor and stator permanent magnet arrangement in such a way as to provide single geometric adjusting degree of freedom which extends, in this case, in the axial direction of the rotor 1. This permanent magnet arrangement which suspends the rotor 1 comprises a permanent annular magnet 17a or 17b which is positioned concentric to the axis 16 of the rotor and is stationary in the stator 5, and comprises a permanent bar magnet 18a or 18b (FIGS. 1 and 2) or a permanent annular magnet 28c or 18d (FIG. 6) which is positioned concentric with the permanent annular magnet 17a, 17b about the axis 16 of the rotor and inside the rotor 1.

In particular, the permanent annular magnet 17a or 17b is magnetized in the axial direction of the rotor 1, as indicated in FIGS. 2 and 6 by the north pole N and the south pole s. Furthermore, the permanent bar magnet 18a or 18b or the permanent annular manget 18c or 18d FIG. 6 of the rotor is staggered axially with respect to the allocated permanent annular magnet 17a or 17b of the stator such that it is positioned just outside the permanent annular magnet 17a or 17b of the stator or just toughes that magnet. In this manner, an optimum radially centering force effect is produced by the permanent magnet arrangement consisting in each case of a permanent annular magnet 17a or 17b in the stator and a permanent bar magnet 18a or 18b or a permanent annular magnet 18c or 18d in the rotor. The permanent bar magnets 18a and 18b or the permanent annular magents 18c and 18d are also magnetized in the axial direction of the rotor (see the details concerning the poles in FIGS. 2 and 6), and the rotate together with the rotor 1 about the rotor axis 16, or may be mounted so that they are freely rotatable in the rotor 1 and such that they do not then rotate with the rotor.

Moreover, each of the two permanent- and electromagnet-magnet arrangements 6a and 6b have an annular electromagnet 19a or 19b inside which the permanent bar magnet or the permanent annular magnet of the rotor is positioned. The electromagnets 19a and 19b are provided concentric to the rotor axis 16 in a stationary manner in the stator 5.

Consequently, the electromagnet 19a or 19b interacts magnetically with the allocated cylindrical permanent bar magnet 18a or 18b or with the permanent annular magnet 18c or 18d of the stator 5, the permanent bar magnet 18a or 18b or the permanent annular magnet 18c or 18d of the stator 5 for its part interacting magnetically with the allocated permanent annular magnet 17a or 17b of the stator. The axial position of the rotor 1 is centered and stabilized by the electromagnets 19a and 19b interacting with the permanent magnets 18a and 18b or 18c and 18d. In symmetry and in the central position, the axial permanent magnetic forces are compensated precisely so that at stable equilibrium is produced.

In order to effect the centering and stabilization, the magnetic field of the two electromagnets 19a and 19b which are connected to the output 21 of the control circuit 7 via corresponding lines 20a or 20b is constantly regulated.

FIG. 6 shows an embodiment of an axial-centrifugal blood pump in which the same reference numerals have been used for those parts which are similar to those in FIGS. 1 & 2. Only the features which differ from those of FIGS. 1 and 2 will be described in the following, but reference will also be made to the description of FIGS. 1 and 2.

Unlike the radial-centrifugal pump described above, the rotor 1 in FIG. 6 is of a tubular design and bladeor screw profiles 100 are provided on the inner periphery of the tube for conveying the blood through the inside thereof, these profiles running to a point at the blood inlet at 100a and at the blood outlet 100b. In this case, instead of the permanent bar magnets 18a and 18b which are provided in FIGS. 1 and 2, permanent annular magnets 18c and 18d which have already been described, are provided in the tube outer casing of the rotor 1 at both axial ends, the same type of polarization (facing oppsoite poles) as in FIGS. 1 and 2 being used (see the poles N and S in FIG. 6).

A backflow of blood against the direction of arrows 14 should preferably be prevented or reduced in the gap 101 between the outer periphery of the rotor 1 and the inner periphery of the stator 5. This may be effected by conveyor blades (not shown) which are provided on the outer periphery of the rotor 1 or in openings which are formed between the permanent annular magnet 18c and/or 18d and a short circuit ring 10c of the rotor 1 and pass through the tubular outer surface of the rotor 1, or by designing these openings as conveying channels extending in screw shape in a radial and axial direction, which convey the blood in the direction of the arrows 14 in the gap 101.

Moreover, stationary deflection paddles 102, 103 may be provided in the blood in-flow channel 3c upstream of the rotor 1 and/or in the blood outlet 4 downstream of the rotor 1, to achieve a satisfactory efficiency.

Figure 5:
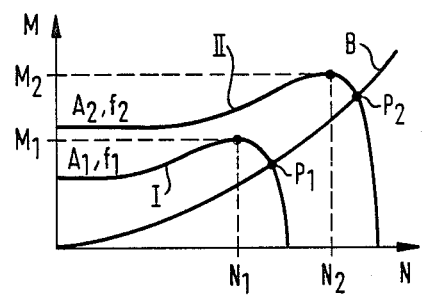
FIG. 5 shows a curve which illustrates an example of the optimum choice for the operating parameters of the asynchronus motor which is used in FIG. 1 as the rotor drive.

To drive the axial-centrifugal blood pump of FIG. 6, a single electromagnet 10 is positioned in the stator 5 instead of the two electromagnets 10a and 10b of FIG. 1, which electromagnet 10 co-operates as an asynchronous motor with the short circuit ring 10c of the rotor 1 in the same manner as explained with reference to FIGS. 1 and 5. Reference numeral 105 indicates the exciter winding of the electromagnet 10.

The pulse radiation barriers 8a and 8b co-operate through bores 104a and 104b in the permanent annular magnet 17a or 17b with the pointed axial ends 23a and 23b of the rotor 1.

The stabilizing and centering control of the axial rotor position in the centrifugal blood pump according to FIGS. 1 and 6 will now be described in more detail.

For this control, the actual value input 22 of the control circuit 7 is connected to the output of the position sensor operating circuit 9 at which a signal is received which represents the actual position of the rotor 1 as sensed by means of the pulse radiation barriers 8a and 8b in co-operation with the axial ends 23a and 23b of the rotor 1.

For the operation thereof, radiation transmitting elements 24a and 24b, for examples an LED diode operating within the infrared range or an ultrasonic transmitter, are coupled via a line 25 to the output of an amplifier 26, the input of which is connected to the output of an oscillator 27. The amplifier 26 and the oscillator 27 belong to the position sensor operating circuit 9, the signal inputs 28a and 28b of which are each connected to one of the radiation receiving elements 29a or 29b of the pulse radiation barriers 8a or 8b. These radiation receiving elements 29a and 29b are preferably an infrared sensor or an ultrasonic sensor.

The control circuit 7, which receives its actual value from the position sensor operating circuit 9 or, in the simplest case, from a position sensor determining the axial position of the rotor 1, controls the electric current intensity in the electromagnets 19a and 19b so that the actual value received at the actual value input 22 finally conforms with a predetermined desired value for the axial position of the rotor 1.

To this end, the control circuit 7 comprises, for example, a pre-amplifier 30 directly connected to the actual value input 22, the output of which amplifier is connected to a subsequent servo amplifier 31 which controls an output amplifier 32 which regulates in a manner proportional to the current. Moreover, the control circuit 7 has a hierarchical or superimposed regulator 33 which is described in more detail in the following.

The servo amplifier 31 is preferably a PDT servo-amplifier, i.e., a proportional-differential servo-amplifier with a time function element. The advantages of this servo-amplifier are, in particular, that system noise is suppressed and the regulating stability is improved.

Figure 4A:
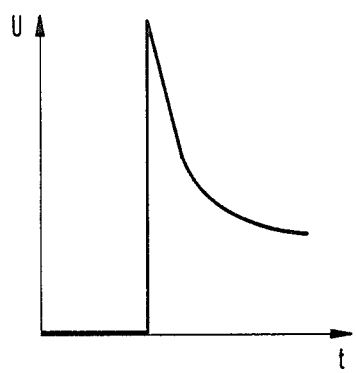
FIGS. 4a and 4b each show curves which indicate the path of the voltage or the current with respect to time which may be achieved on the winding of the electromagnet which is connected to the output stage shown in FIG. 3.
Figure 4B:
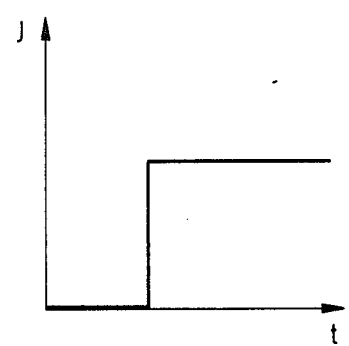

The output amplifier 32 converts a given input voltage into a proportional output current, and that is, independently of the electrical load conditions. In this manner, almost instantaneously, i.e. for example step-shaped increases in current may be achieved in spite of the relatively great inductance of the regulated electromagnets 19a and 19b, in that the voltage, as shown in FIG. 4a is initially increased to a substantially greater extent than corresponds to the desired increase in current, and then reduced relatively quickly to a voltage value which actually corresponds to the desired current.

Figure 3:
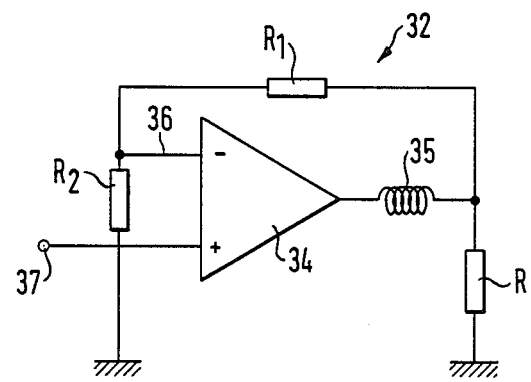
FIG. 3 shows a preferred embodiment of a proportional control output stage which is provided in the control circuit of the magnetic rotor bearing according to FIG. 1.

An example of an output amplifier 32 which regulates in a manner proportional to the current is shown in FIG. 3. This output amplifier 32 comprises an operational amplifier 34 the output of which is earthed via the magnetic field coil 35 provided as the load, of the electromagnet 19a or 19b and a low-value resistor R. The voltage drop at the resistor R which is proportional to the current through the magnetic field coil 35 is returned via a voltage divider formed by resistors $R_1$ and $R_2$, to the negative input 36 of the operational amplifier 34 which may also be termed the negative feedback input. The positive input 37 of the operational amplifier 34 is coupled to the output of the servo amplifier 31.

The construction and operation of the pulse radiation barriers 8a and 8b and of the position sensor operating circuit 9 will now be described.

As already mentioned, the pulse radiation barrier 8a co-operates with one axial end 23a of the rotor 1, so that depending on the axial position of the rotor, radiation from the radiation transmitting element 24a, as indicated by the two small arrows, may arrive at the allocated radiation receiving element 29a or is hindered by the axial end 23a of the rotor 1 from falling on the radiation receiving element 29a. Accordingly, the radiation transmitting element 24b and the radiation receiving element 29b co-operates with the other axial end 23b of the rotor. In the present case, infrared radiation transmitting elements are provided as radiation transmitting elements and infrared radiation receiving elements are provided as radiation receiving elements.

The oscillator 27 which may also be, for example quite generally a pulse generator, preferably has a frequency in the range of from 10 to 100 kHz, amounting more preferably to 40 kHz. The infrared radiation transmitting elements are selected so that they produce infrared radiation in a wavelength region in which blood has a low absorbtivity, i.e., about 1 μm.

It is pointed out with respect to the above-mentioned frequency range of the oscillator 27, that the systme would react too slowly if the pulse frequency was selected to be substantially lower than 10 kHz, and that is, on account of the signal processing in the integrator which is described later on. On the other hand, if the pulse frequency of the oscillator 27 is selected to be substantially higher than 100 kHz, the electro-optical efficiency of the light-emitting diodes used as infrared radiation transmitting elements is unfavorable and the evaluation is complicated by high-frequency effects.

The infrared radiation receiving elements are preferably photodiodes or phototransistors, the maximum spectral sensitivity of which lies in the same range as the maximum emitting power of the infrared radiation transmitting elements.

The part of the position sensor operating circuit 9 by which the output signals of the radiation receiving elements 29a and 29b are processed into the actual value to be supplied to the input 22 of the control circuit 7, comprises a subtraction device 38 which subtracts the signals emitted by the two radiation receiving elements 29a and 29b from each other, and a subsequently connected integration device 39. A sample- and hold circuit 40 is connected downstream of this integration device 39. Moreover, a first switch S1 is provided between the output of the subtraction device 38 and the input of the integration device 39. A second switch S2 is provided between the reset connection 41 of the integration device 39 and earth and is used for resetting the integration device 39 in each case. Finally, a third switch S3 is positioned between the output of the integration device 39 and the input of the sample- and hold circuit 40, the output of which is coupled to the actual value input 22 of the control circuit. To control the closing and opening of the switches S1, S2 and S3, a delivery control device 42 is provided in the position sensor operating circuit 9 which receives input signals from the oscillator 27 synchronously with the signals which arrive at the signal inputs 28a and 28b because the switches S1, S2 and S3 are opened and closed in a manner which is described in more detail later on.

So that the position sensor operating circuit 9 does not simply integrate with the electrical impulses released by the radiation receiving elements 29a and/or 29b and based on the radiation pulses, with a high time constant, which would imply a response delay in the entire control of the electromagnets 19a and 19b and thus could possibly lead to natural oscillations or to the position of the rotor no longer being guaranteed through the effect of rapid external forces, the construction and operation of the position sensor operating circuit 9 is as will now be described in detail in the following.

First of all, the subtraction device 38 which has already been mentioned is connected between the radiation receiving elements 29a and 29b which, when infrared radiation is used, are for example phototransistors or photodiodes or other photoreceivers, and the integration device 39 which simultaneously operates as a pre-amplifier. This subtraction device 38 subtracts the output signals of the radiation receiving elements 29a and 29b, and has, in particular, the following purpose and the following advantages:

(a) Any disturbance by foreign radiation is reduced, and that is, in particular because possible foreign radiation which comes from outside has effect to approximately the same or to a similar intensity at both radiation receiving elements 29a and 29b and during the subtraction of the signals of these radiation receiving elements, the proportion of the foreign radiation is mutually cancelled out completely or to a substantial extent. Moreover, the likelihood of foreign radiation of precisely 40 kHz and in proper phse disturbing the transmitted signal is very small.

(b) The working range of the complete sensor arrangement is expanded, as regards determining the axial position of the rotor 1, and that is, in connection with the arrangement of the pulse radiation barriers 8a and 8b, such that these pulse radiation barriers overlap only in a small working range, i.e. the transition regions between the complete closing condition and the complete opening condition of these two pulse radiation barriers 8a and 8b, which do not completely coincide, but overlap in a small area only with respect to the complete transition region in each case, which means that the two pulse radiation barriers 8a and 8b are simultaneously located in this their transition region only over a short length of their transition region.

(c) As a result of the subtraction of the output signals of the two radiation receiving elements 29a and 29b, the characteristic line of the position sensor arrangement, i.e., of the complete arrangement of the pulse radiation barriers 8a and 8b and the position sensor operating circuit 9 is linearised in the overlapping working region which is defined above.

The integration device 39 operates such that it integrates the difference pulses obtained at the output of the subtraction device 38 which are obtained by the subtraction of the pulse-shaped output signals of the radiation receiving elements 29a and 29b, in a periodic manner only via, in each case, a few individual difference pulses, for example four differences pulses, and then passes this integration value on to the sample-and hold circuit 40 at its output via the switch S3. the integration may be an amplitude integration which is independent of the width of the difference pulses. The integration time constant may be selected to be very high, i.e., it may tend towards infinity.

The following advantages in particular are obtained by this type of further processing of the difference pulses in the integration device 39:

(1) In spite of the very high integration time constants of the integration device 39, the entire position sensor arrangement reacts almost immediately, i.e., after a few individual difference pulses, for example, after four difference pulses, to a change in amplitude, so that the position sensor arrangement responds very quickly to axial changes in position of the rotor 1, because the pulse repetition frequency lies simultaneously in the range of from 10 to 100 kHz, preferably at 40 kHz, as mentioned above. In the case of the above-mentioned preferred pulse repetition frequency, the response time therefore amounts to about 10 msec. This response time may be extended or shortened as required, depending on the practical requirements, by changing the pulse repetition frequency and/or the number of periodically integrated individual difference pulses, and thus may be adjusted in an optimum manner.

(2) Since no relatively great changes in the axial position of the rotor 1 are usually produced, conditioned alone by the inertia of the rotor 1 within the above-mentioned short response time of the entire position sensor arrangement, the change in the actual value which appears at the actual value input 22 is virtually the same as the integrated value, and thus the regulation of the electromagnets 19a and 19b by the control circuit 7 to a new value of the integrated amplitude of the difference pulses do not take place abruptly, but gradually on account of the method of integration which is used, so that no actual value jumps take place by which natural oscillations could be excited.

In the sample- and hold circuit 40, the integration value obtained at the output of the integration device 39 is firmly retained in each case and passed on to the actual value input 22 as an actual value until the sample-and hold circuit 40 is supplied with a new integration value by the integration device 39 via the switch S3.

The delivery control device 42 opens and closes the switches S1, S2 and S3 in the following manner, to which end it receives its clock frequency via a line 43 from the pulse generator or oscillator 27.

(a) The first switch S1 is always closed when the radiation transmitting elements 24a and 24b are connection and thus the radiation receiving element 29a and/or 29b releases an output signal, i.e., a difference pulse is generated at the output of the subtraction device 38. However, in the interval between the appearance of successive difference pulses, the switch S1 is opened. This means that the difference pulses of the subtraction device are passed on to the integration device 39 synchronously with the pulse operation of the pulse radiation barriers 8a and 8b. In this manner, the influence of possible disturbing radiation is substantially reduced.

(b) The third switch S3 is closed after, in each case, a predetermined number of difference pulses, for example, after in each case four difference pulses, so that each of the integration values which are received periodically by the integration device 39, is passed on to the sample- and hold circuit 40 and thus is made available as an actual value for the control circuit.

(c) After the respective integration value has been passed on to the sample- and hold circuit 40 by closing the switch S3 and the switch S3 has been reopened, the second switch S2 is closed in order to cancel the old integration value in the integration device 39.

(d) The second switch S2 and the third switch S3 are preferably closed in each case only within an opening period of the first switch S1. However, the switches S2 an S3 may also be closed for a longer period, but they may never be closed at the same time, but the switch S3 must always be closed before the switch S2, and the switch S2 must only be closed after the switch S3 has been opened, so that a zero integration value is not released to the sample- and hold circuit 40 and thus a completely false and, moreover, an irregularly changed actual value, is not received at the actual value input 22. As long as the switch S2 is closed while observing these conditions, no further integration takes place, so that, due to a longer closing period of the switch S2, the response time of the complete position sensor arrangement to axial changes in position of the rotor 1 may be prolonged. If the switch S3 is kept closed for a longer period while observing the above-mentioned conditions, the number of the periodically amplitude-integrated difference pulses is consequently increased, i.e., the response time of the complete position sensor arrangement is also prolonged.

The delivery control device 42 is preferably a digital control device, particularly because it is used to operate the switches S1, S2 and S3 which in each case have only two conditions, namely an open and a closed condition.

The general principle on which the position sensor operating circuit 9 described above is based consequently resides in the fact that the position sensors, in the present case the pulse radiation barriers 8a and 8b, which are used for determining the axial position of the rotor 1 are operated in terms of pulses, disturbances are eliminated by forming the difference of the position sensor signals, the difference pulses are integrated intermittently over in each case only a few individual difference pulses, the difference pulses to be integrated in the integration device are delivered synchronously with the appearance of the radiation pulses in the position sensors, and the integration value which is determined intermittently is also held at the output of the position sensor operating circuit 9 and thus at the actual value input 22 of the control circuit 7 in the intervening periods between two integration intervals.

A possible influence of disturbing radiation on the position sensors and thus on the actual value of the control circuit is eliminated as a whole in particular by the following measures:

(1) by pairing narrow-band radiation transmitting elements 24a and 24b with narrow-band radiation receiving elements 29a and 29b, for example by pairing narrow-band infrared radiation transmitting elements and infrared radiation receiving elements, the main radiation transmitting- or receiving elements preferably using infrared radiation which lies at a wavelength of about 1 μm;

(2) by a capacitive coupling which has been mentioned above, with low time constants between the radiation receiving elements 29a and 29b on the one hand and the subtraction device 38 on the other hand, i.e., by a differential element which only allows through rapid voltage changes;

(3) by the subtraction device 38, as described above in in more detail;

(4) by a synchronised take-over of the difference pulses from the subtraction device 38 into the integration device by means of a suitable delivery control, as described above; and (5) by the periodic integration of, in each case, only several individual difference pulses, for example four difference pulses; consequently, even the effect of possible, very short-term disturbances, the duration of which is of the order of magnitude of the duration of an individual difference pulse or shorter, is eliminated, because while a portion caused by such a short-time disturbance may be considerable with respect to a single difference pulse, it may be reduced by amplitude integration of several different pulses.

The construction and operating method of the superimposed regulator 33 will now be described.

The superimposed regulator 33 comprises a detection device 44 which detects the presence of external forces, and also comprises a adjusting device 45 which moves the rotor 1 out of its centre position which is stabilized in the axial direction, into an axially eccentric stabilization position during the effect of external forces, and comprises a comparison device 46 which compares the energy requirement of the rotor bearing in the rotor 1 located in an axial direction in the stabilized centre position with the energy requirement of the rotor bearing when the rotor 1 is located in an axial direction in an eccentric stabilization position.

In particular, the detection device 44 may be, for example, a current meter which measures the electric current flowing through the electromagnets 19a and 19b. Consequently, in the view of FIG. 1, the detection device is connected to the output of the output amplifier 32 or to the electromagnets 19a and 19b via lines 47a and 47b. Alternately, the detection device 44 may also be a current meter which measures the electric current flowing through the entire control loop which comprises the position sensor arrangement, the remaining part of the control circuit and the electromagnet arrangement. A further alternative is for the detection device 44 to comprise an acceleration sensor which detects the axial orientation or, generally, the direction of a respective external force.

In the present case, the detection device 44 is connected to the adjusting device 45 via the comparison device 46, because it detects the external forces by determining the energy requirement of the rotor bearing and thus not only determines the energy requirements of the rotor bearing in the axially stabilized centre position of the rotor, but also the energy requirement of the eccentric axial stabilization position of the rotor, and delivers the quantities to the comparison device 46 which compares them. If, on the other hand, the detection device 44 directly determines the external forces, for example by an acceleration sensor, without determining the energy requirement of the rotor bearing, it may be directly connected to the adjusting device 45, in which case another detection device is provided for determining the respective energy requirement or a quantity proportional to this energy requirement and delivers to the comparison device 46 the energy requirement values of the rotor bearing to be compared.

In the latter case, the adjusting device 45 is a control device which responds to the output signal of the detection device 44 and to the output signal of the comparison device 46 and which releases a signal, for example, a voltage at its output, by which the desired value for the axial position of the rotor 1 is modified via a line 48 which leads to the pre-amplifier 30 or to the servo-amplifier 31. The desired value is modified either directly or indirectly in that a quantity modifying the actual value is added to, or subtracted from the actual value obtained at the actual value input 22, which corresponds to a desired value displacement. In the circuitry according to FIG. 1, the adjusting device 45 is only connected to the output of the comparison device 46, because the detection device 44 does not simply determine the presence of external forces, but rather the energy requirement of the rotor bearing, so that an increase in this energy requirement is established by the comparison device and a corresponding output signal is released by the latter to the adjusting device which causes the adjusting device 45 to move the rotor axially. In any case, the axial movement of the rotor takes place by an increase or a reduction in the current flowing through the electromagnets 19a and 19b as a result of the desired value modification.

The comparison device 46 may comprise, for example a sample- and hold circuit which compares the energy- or power requirement values of the electromagnets 19a and 19b and of the entire control loop which, in the present case, are determined by the detection device 44, in different axial positions of the rotor 1, and, based on this comparison, releases an output signal to the adjusting device 46 which causes the device 45 to shift the axial position of the rotor 1 in the sensor of lower energy-or power requirement values of the electromagnets 19a and 19b. To this end, the comparison device 46 has a memory which stores the previous energy- or power requirement, so that it may be compared with a new energy- or power requirement. In this manner, the axial position of the rotor 1 may be adjusted gradually by successive energy- and power requirement comparisons and by successive modifications of the desired value for the axial rotor position by in each case, small amounts, until the energy- or power requirement has reached its minimum.

The purpose of the superimposed regulator 33 is to vary the desired value of the rotor position along the degree of freedom stabilized by the electromagnetis, i.e., in the present case, in an axial direction, during the long-term effect of external forces, so that the energy consumption of the position control or of the magnetic position stabilization of the rotor 1 is reduced, preferably minimized.

As described above in the general part of the description, this energy consumption may consequently be reduced by a factor of about 100 to 150.

The general method by which this is effected and which is realized in the arrangement according to FIG. 1 is summarized in the following:

(a) the presence of external forces is detected;

(b) the rotor is moved from its stabilized centre position into a new stabilization position, and (c) it is established whether the new stabilization position results in a lower energy requirement for the magnetic bearing of the rotor; this lower energy requirement results if the new stabilization position is such that the permanent magnets which are provided in addition to the electromagnets for the magnetic rotor bearing produce a counter-force to the detected external force;

(d) the stabilization position of the rotor is changed until a reduced, preferably minimized energy requirement for the rotor bearing is established.

In the above-mentioned step (b), instead of the rotor being moved in the first step with a restricted step width, in an arbitrary manner in any direction out of its stabilized centre position, it may also be moved in the first step in the sense of a reduction of the energy requirement, as long as not only the presence of the external force, but also the direction thereof (positive or negative) in the direction of the degree of freedom which is stabilized by the electromagnets is established by the detection device. If, moveover, the detection device also determines the magnitude of the external force which appears in the direction of the above-mentioned degree of freedom, a gradual change in the stabilization position of the rotor may be omitted, and the rotor may be moved in one step into its new stabilization position corresponding to a minimum energy requirement of the magnetic rotor bearing, while it is programmed according to the direction and magnitude of the force component which acts along the stabilized degree of freedom.

The rotary drive of the rotor 1 will now be described in more detail with reference to the upper part of FIG. 1 and with reference to FIGS. 5 and 6.

This rotary drive may be designed in a variety of ways, for example as an eddy current drive, in particular by means of an asynchronous motor, as a synchronous motor, as an electrically commutated electromotor or the like. An asynchronous motor is preferably provided as the drive of the rotor 1 and it comprises the annular driving electromagnets 10a, 10b (FIG. 1) or 10 (FIG. 6) in the stator 5, and the rotor 1 as a squirrel-cage rotor (FIG. 1) or a squirrel-cage rotor ring short circuit 10c (FIG. 6) and the three-phase driving electromagnets 10a, 10b or the driving electromagnet 10, the windings of which function as field excitation coils. These windings which are not shown in FIG. 1 and are indicated in FIG. 6 by reference numeral 105 are preferably connected in a star-connection with a phase shift of $\rho = 60°$. The potential gradients on 49a 49b and 49c which lead to the windings of the driving magnets 10a, 10b or 10, follow the expressions given in FIG. 1 at these supply lines, where A represents the maximum voltage amplitude, f represent the frequency of the alternating voltage and $\rho$ represents the above-mentioned phase displacement of the three phases 1, 2 and 3 on the supply lines 49a, 49b and 49c with respect to one another.

An oscillator 50 is provided as the operating voltage source, to which the supply lines 49a, 49b and 49c are connected via lines 51a, 51b and 51c and a respective power amplifier 52a, 52b and 52c whose amplification level may be controlled and which amplifies the alternating voltage supplied by the oscillator 50. The degree of amplification, and thus the output amplitude A of the alternating voltage received at the output of the power amplifiers 52a, 52b and 52c is controlled by means of a control voltage which is supplied via line 53 to amplification level-control inputs. The frequency of the oscillator 50 may also be changed and may be adjusted via a corresponding control voltage which is supplied to the frequency-control input 55 of the oscillator 50. In this manner, the frequency f and the output voltage amplitude A of the oscillator on the windings of the driving electromagnets 10a and 10b or 10 may be changed.

This change in the frequency and the output voltage amplitude takes place in a pre-determined or programmed manner by means of a first characteristic memory 56, the output of which is coupled to the frequency-control input 55 of the oscillator 50, and by means of a second characteristic memory 57, the output of which is coupled to the amplification level-control inputs 54a, 54b and 54c of the power amplifiers. The input of the second characteristic memory 57 is connected to an output of the oscillator 50 via a frequency-to-voltage converter 58. In this manner, the amplitude A is changed depending on the respective operating frequency f which the oscillator 50 produces according to a predetermined characteristic which is indicated symbolically on the characteristic memory 57.

To control the frequency f of the oscillator 50 with the first characteristic memory 56, a control signal is given to the input 59 of the latter which may be produced in a variety of ways. In the present case of the control or regulation of the drive of a blood pump, namely the centrifugal blood pump 2, this control signal is produced by pressure sensor 12 and is delivered via a line 60. This pressure sensor produces an output voltage representing the pressure on the venous side or on the suction side of the blood pump, as the control signal. This output voltage is converted by the first characteristic memory 56 according to a Frank-Starling characteristic into a corresponding control voltage for the oscillator 50, such that the pump characteristic of the centrifugal pump 2 acting as an artificial heart corresponds to the physiological conditions, as specified by Frank and Starling via a relation usually known as Starlings law as specified for example in the medical dictionary of Pschyrembel, published by Walter De Gruyter, Berlin and New York, 1972.

To this end, the characteristic memory 56 clearly allocates a specific control voltage 55 at its output to a predetermined control signal at its input 59, the memory 56 passing this control voltage 55 on to the frequency-control input of the oscillator 50, as mentioned.

The second characteristic memory 57 has a characteristic such that the operating voltages obtained on the supply lines 49a, 49b and 49c are varied in their frequency f and their output voltage amplitude A depending on the load and speed, such that the torque provided by the asynchronous motor, i.e. in the present case the torque produced at the rotor 1, correlates with the moment of load in the case of the respective speed of the asynchronous motor, i.e. in the present case, of the rotor 1.

In a particularly favourable and preferred embodiement which will now be described using the simple drawing of FIG. 5, the respective moment of load of the rotor on the motor characteristic line I or II of the asynchronous motor lies just below the breakdown torque and above the breakdown speed. FIG. 5 shows two selected motor characteristic line I and II which apply in each case to an output voltage amplitude $A_1$ or $A_2$ and an allocated frequency $f_1$ or $f_2$, and that is, the motor characteristic line represents in a conventional manner the torque M depending on the speed N (for example in revolutions per minute) of the asynchronous motor.

The points $P_1$ and $P_2$ on the operating characteristic line B of the motor obtained lie, according to the above-mentioned definition of this selected operating line, in each case just below the breakdown torque $M_1$ or $M_2$ and above the breakdown speed $N_1$ or $N_2$ of the motor characteristic line I or II valid for the relevant output voltage amplitude $A_1$ or $A_2$ and for the relevant frequency $f_1$ and $f_2$. This applies to all other points on the operating characteristic line B of the asynchronous motor.

In this manner, the rotor 1 of the centrifugal blood pump 2 is driven at a minimum expenditure of energy and at the same time, the actual blood pumping power corresponds to the Frank-Starling characteristic, i.e., is adapted optimally to the physiological conditions of the human blood circulation. The characteristic memories 56 and 57 provided for this purpose may be, for example a resistor network matrix or an electronic memory, considering the fact that the respective characteristic is non-linear.

The magnetic rotor bearing according to the present invention has in particular, the not exclusively, the following advantages:

(a) it manages to operate at the lowest energy requirement.

(b) it remains operative in particular where it is provided in moving parts, devices or the like, for example rockets, in spite of the movement of the respective device, in particular despite the acceleration or delay thereof, so that it may be used without restriction in all cases in which the stator as such undergoes a movement.

(c) It may also be widely used in particular on account of the advantages specified above under (a) and (b), where it has to operate with a non-recurring energy supply which cannot be supplemented during operation, i.e. in so-called insular operation.

We claim:

1. An absolutely-low energy consuming, and relatively-high electromagnetically efficient, magnetic rotor bearing assembly, comprising:

a stator;

a rotor having an axis of rotation that is disposed in the stator;

said rotor has a shaft, wherein the rotor and its shaft are hollow inside, and have a total density selected to be exactly adapted to that of human blood;

permanent first magnet means including a permanent magnet mounted to the rotor cooperative with a permanent magnet mounted to the stator for magnetically suspending said rotor in said stator by magnetic repulsion so that the rotor is free from mechanical contact with the stator and is axially movable by displacement along the axis of rotation, the permanent magnet mounted to the rotor is axially staggered with respect to the permanent magnet mounted to the stator to maximize centering forces;

second magnet means including a permanent magnet mounted to the rotor cooperative with an electromagnet having a field intensity mounted to the stator for stabilizing the rotor against displacement along the axis of rotation; and means coupled to the second magnet means responsive to a desired value representing an intended axial position of the rotor and including a position sensor providing a signal respresentative of actual axial position of the rotor for providing a field intensity of the electromagnet of the second magnet means such that the rotor is always axially moved from its actual position to the intended axial position in the absence of symmetrical external forces.

2. An absolutely-low energy consuming, and relatively-high electromagnetically efficient, magnetic rotor bearing assembly, comprising:

a stator;

a rotor having an axis of rotation that is disposed in the stator;

permanent first magnet means including a permanent magnet mounted to the rotor cooperative with a permanent magnet mounted to the stator for magnetically suspending said rotor in said stator by magnetic repulsion so that the rotor is free from mechanical contact with the stator and is axially movable by displacement along the axis of rotation, the permanent magnet mounted to the rotor is axially staggered with respect to the permanent magnet mounted to the stator to maximize centering forces;

second magnet means including a permanent magnet mounted to the rotor cooperative with an electromagnet having a field intensity mounted to the stator for stabilizing the rotor against displacement along the axis of rotation;

means coupled to the second magnet means responsive to a desired value representing an intended axial position of the rotor and including a position sensor providing a signal representative of actual axial position of the rotor for providing a field intensity of the elctromagnet of the second magnet means such that the rotor is always axially moved from its actual position to the intended axial position in the absence of symmetrical external forces;

said position sensor includes at least one pulsed radiation barrier having a pulsed radiation transmitting element and a cooperative radiation receiving element; and further including another pulsed radiation barrier that includes a pulsed radiation transmitting element and a pulsed radiation receiving element, said pulsed radiation barriers being mounted to respective axial ends of the rotor, said pulsed radiation receiving elements providing respective output signals, a subtraction device having an input and an output for subtracting the output signals of the radiation receiving elements of the two pulsed radiation barriers, an integration device having an input and an output for integrating the output signal of the subtraction device, a sample and hold circuit an input of which is connected to the output of the integration device, a first switch coupled between the output of the subtraction device and the input of the integration device, a second switch connected to the integration device for resetting the integration device, a third switch connected between the output of the integration device and the input of the sample and hold circuit, and a control for controlling the duty cycles of the three switches such that the first switch is always closed when the radiation transmitting elements are transmitting, the third switch is closed in each case after the integration of a predetermined number of output signals from the subtraction device, and the second switch is closed as soon as the third switch has been opened.

3. An absolutely-low energy consuming, and relatively-high electromagnetically efficient, magnetic rotor bearing assembly, comprising:
   a stator;
   a rotor having an axis of rotation that is disposed in the stator;
   permanent first magnet means including a permanent magnet mounted to the rotor cooperative with a permanent magnet mounted to the stator for magnetically suspending said rotor in said stator by magnetic repulsion so that the rotor is free from mechanical contact with the stator and axially movable by displacement along the axis of rotation, the permanent magnet mounted to the rotor is axially staggered with respect to the permanent magnet mounted to the stator to maximize centering forces;
   second magnet means including a permanent magnet mounted to the rotor cooperative with an electromagnet having a field intensity mounted to the stator for stabilizing the rotor against displacement along the axis of rotation; and
   means coupled to the second magnet means responsive to a desired value representing an intended axial position of the rotor and including a position sensor providing a signal representative of actual axial position of the rotor for providing a field intensity of the electromagnet of the second magnet means such that the rotor is always axially moved from its actual position to the intended axial position in the absence of asymmetrical external forces;
   said rotor is adapted to operation as a conveying member in a blood pump having a suction side, and further including a power control device, said power control device including a pressure sensor on the suction side of the blood pump, and a characteristic memory having its input connected to the pressure sensor, said memory providing predetermined output signals in response to a predetermined input signal, and a power control device for controlling the pumping power in response to the output signal of the characteristic memory.

4. The assembly of claim 3, wherein the power control device includes an oscillator having a frequency and an output voltage coupled to the asynchronous motor of the blood pump, and means for changing the frequency and output voltage of the oscillator depending on the load and speed of the blood pump.

5. The assembly of claim 4, further including a second characteristic memory connected between the asynchronous motor and the oscillator for changing the operating voltage amplitude of the asynchronous motor depending on the frequency of the oscillator.

* * * * *

UNITED STATES PATENT AND TRADEMARK OFFICE
CERTIFICATE OF CORRECTION

PATENT NO. : 4,763,032

DATED : August 9, 1988

INVENTOR(S) : Gunter Bramm; Pavel Novak

It is certified that error appears in the above-identified patent and that said Letters Patent is hereby corrected as shown below:

Column 1, line 39, "radioactiveliquids," should read --radioactive liquids,-- line 58, "electromagnetics" should read --electromagnets-- line 68, "built-up" should read --build-up--

Column 2, line 50, "a high" should read --as high--

Column 4, line 14, "magnetic" should read --magnet-- line 23, "as the same kind of" should read --of the same kind as-- line 56, "magnetic length." should read --magnet length.--

Column 5, line 31, "particular" should read --particularly-- line 58, "motor" should read --rotor--

Column 6, line 11, "hse," should read --has,-- line 34, "deivce" should read --device-- line 61, "currnet" should read --current--

Column 7, line 44, "nbarrier" should read --barrier--

Column 10, line 13, "as" should read --an-- line 31, "pressur" should read --pressure-- line 46, "FIG. 1" should read --(FIG. 1)-- line 56, "28c" should read --18c-- line 62, "pole s." should read --pole S.-- line 63, "manget" should read --magnet-- line 64, "FIG. 6" should read --(FIG. 6)-- line 68, "toughes" should read --touches--

UNITED STATES PATENT AND TRADEMARK OFFICE
CERTIFICATE OF CORRECTION

PATENT NO. : 4,763,032

DATED : August 9, 1988

INVENTOR(S) : Gunter Bramm; Pavel Novak

It is certified that error appears in the above-identified patent and that said Letters Patent is hereby corrected as shown below:

| | | |
|---|---|---|
| Column 11, | line 6, | "magents" should read --magnets-- |
| | line 14, | "magnet magnet" should read --magnet-- |
| | line 32, | "at stable" should read --a stable-- |
| | line 56, | "oppsoite" should read --opposite-- |
| Column 13, | line 44, | "systme" should read --system-- |
| Column 14, | line 48, | "phse" should read --phase-- |
| Column 15, | line 11, | "S3. the" should read --S3. The-- |
| | line 30, | "10 msec." should read --0.10 msec.-- |
| | lines 60-61, | "connection" should read --connected-- |
| Column 17, | line 29, | "a adjusting" should read --an adjusting-- |
| Column 18, | line 37, | "device 46" should read --device 45-- |
| | line 52, | "electromagnetis," should read --electromagnets,-- |
| Column 20, | lines 56-57, | "embodiement" should read --embodiment-- |

UNITED STATES PATENT AND TRADEMARK OFFICE
CERTIFICATE OF CORRECTION

PATENT NO.  : 4,763,032

DATED       : August 9, 1988

INVENTOR(S) : Gunter Bramm; Pavel Novak

It is certified that error appears in the above-identified patent and that said Letters Patent is hereby corrected as shown below:

Column 20, line 62, "line I" should read --lines I--

Column 20, line 64, "$f_2$, and that is, the" should read --$f_2$, the--

Column 22, line 33, "elctromagnet" should read --electromagnet--

Signed and Sealed this

Third Day of September, 1991

*Attest:*

HARRY F. MANBECK, JR.

*Attesting Officer*     *Commissioner of Patents and Trademarks*